(12) United States Patent
Katra

(10) Patent No.: US 8,892,204 B2
(45) Date of Patent: Nov. 18, 2014

(54) AORTIC PACING TO CONTROL CARDIAC AFTERLOAD

(75) Inventor: Rodolphe Katra, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/325,153

(22) Filed: Dec. 14, 2011

(65) Prior Publication Data

US 2012/0158082 A1 Jun. 21, 2012

Related U.S. Application Data

(60) Provisional application No. 61/424,227, filed on Dec. 17, 2010.

(51) Int. Cl.
| | | |
|---|---|---|
| *A61N 1/08* | (2006.01) | |
| *A61N 1/36* | (2006.01) | |
| *A61N 1/362* | (2006.01) | |
| *A61N 1/372* | (2006.01) | |
| *A61B 5/029* | (2006.01) | |
| *A61N 1/365* | (2006.01) | |
| *A61B 5/02* | (2006.01) | |

(52) U.S. Cl.
CPC ........... *A61N 1/3627* (2013.01); *A61N 1/37258* (2013.01); *A61B 5/029* (2013.01); *A61N 1/36114* (2013.01); *A61N 1/36564* (2013.01); *A61N 1/36117* (2013.01); *A61B 5/02028* (2013.01)

USPC ........................................................ 607/17

(58) Field of Classification Search
None
See application file for complete search history.

(56) References Cited

U.S. PATENT DOCUMENTS

| | | |
|---|---|---|
| 5,213,098 A | 5/1993 | Bennett |
| 6,044,297 A | 3/2000 | Sheldon |
| 6,070,101 A | 5/2000 | Struble |
| 6,221,024 B1 | 4/2001 | Miesel |
| 6,529,771 B1 | 3/2003 | Kieval |
| 6,738,667 B2 | 5/2004 | Deno |
| 6,871,088 B2 | 3/2005 | Chinchoy |
| 7,682,316 B2 | 3/2010 | Anderson |
| 2005/0021370 A1 * | 1/2005 | Riff et al. .......................... 705/2 |
| 2007/0299477 A1 * | 12/2007 | Kleckner et al. .................. 607/9 |
| 2008/0058656 A1 * | 3/2008 | Costello et al. ............... 600/508 |
| 2009/0124867 A1 * | 5/2009 | Hirsh et al. .................... 600/301 |
| 2009/0131804 A1 * | 5/2009 | Mukkamala et al. ......... 600/485 |
| 2009/0287267 A1 * | 11/2009 | Wenzel et al. .................... 607/9 |
| 2009/0299423 A1 * | 12/2009 | Min ................................... 607/9 |
| 2010/0023088 A1 * | 1/2010 | Stack et al. .................... 607/44 |

* cited by examiner

*Primary Examiner* — Carl H Layno
*Assistant Examiner* — Ankit Tejani
(74) *Attorney, Agent, or Firm* — Carol F. Barry

(57) ABSTRACT

A chronically implanted medical device, connected to a medical electrical lead that includes a sensor, is used to detect cardiac afterload. Electrical stimulation is delivered proximate to aortic arch tissue of a patient in order to reduce a patient's cardiac afterload. Electrical stimulation is terminated after a termination condition is met.

18 Claims, 6 Drawing Sheets

US 8,892,204 B2

AORTIC PACING TO CONTROL CARDIAC AFTERLOAD

CROSS-REFERENCE TO RELATED APPLICATIONS

This application claims the benefit of U.S. Provisional Application No. 61/424,227, filed on Dec. 17, 2010. The disclosure of the above application is incorporated herein by reference in its entirety.

TECHNICAL FIELD

The present disclosure relates generally to implantable medical devices, and, more particularly, to an implantable medical device that can deliver electrical stimuli to tissue of the aorta.

BACKGROUND

Patients with diastolic heart failure, hypertension and hypertrophy can exhibit elevated cardiac afterload. Cardiac afterload, the impedance to ventricular emptying by aortic pressure, can substantially determine regulation of cardiac output. Cardiac output is the volume of blood flow from the heart which is the heart rate (i.e. the rate of contraction) multiplied by the stroke volume which is the amount of blood pumped out from the heart with each contraction. A high cardiac afterload significantly reduces cardiac output whereas a reduced cardiac afterload increases cardiac output.

Current therapies rely on drugs to reduce cardiac afterload. At least two disadvantages are associated with drugs to reduce cardiac afterload. First, while drugs have had limited success, some patients are nonresponders. Second, chronic use of drugs to reduce cardiac afterload have some undesirable side affects. Therefore, it is desirable to develop therapies that overcome the disadvantages associated with drugs.

SUMMARY

A patient with elevated cardiac afterload can achieve improved cardiac function through pacing of aortic tissue. Pacing aortic tissue can also reduce heart rate. To pace the aortic arch, an implantable medical device with a medical electrical lead extending therefrom can be coupled or screwed into a wall of the aortic arch. In one embodiment, a medical electrical lead is secured to the wall of the aortic arch proximal to the second arterial bifurcation. Pacing can be conducted in a tip to housing or can configuration or through a local bipole configuration. Stimulating the aorta manipulates the heart's contractility thereby affecting pressure and volume.

In one or more embodiments, aortic pacing can be applied after ventricular activation with a timing delay that optimizes ventricular filling and ejection. By reducing afterload, ventricular filling is accelerated and cardiac output is increased without deleteriously affecting heart rate.

In one or more embodiments, aortic pacing can be a stand alone therapy for patients with high cardiac afterload. In one or more other embodiments, aortic pacing can be used during cardiac resynchronization therapy. In yet other embodiments, aortic pacing can be delivered through a medical electrical lead connected to an implantable cardioverter-defibrillator.

In one or more embodiments, a medical electrical lead, placed in the aorta, can have a sensor such as a pressure sensor, to sense high afterload and pressure gradients in the aorta.

DETAILED DESCRIPTION

In the following description, references are made to illustrative embodiments for carrying out the invention. It is understood that other embodiments may be utilized without departing from the scope of the present disclosure.

Figure 1A:
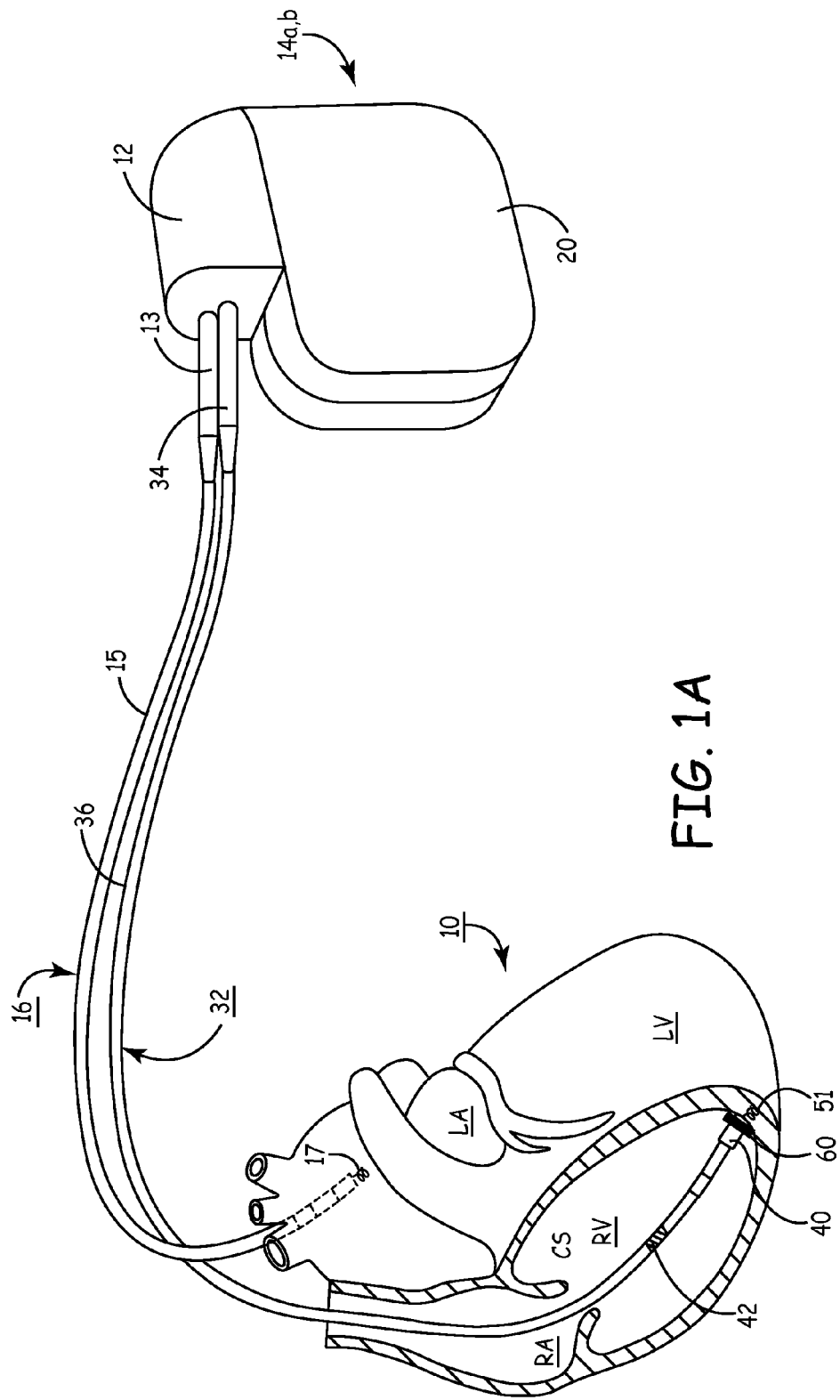
FIG. 1A depicts an implantable, multi-chamber cardiac pacemaker in which one embodiment of the present disclosure may be implemented.
Figure 1B:
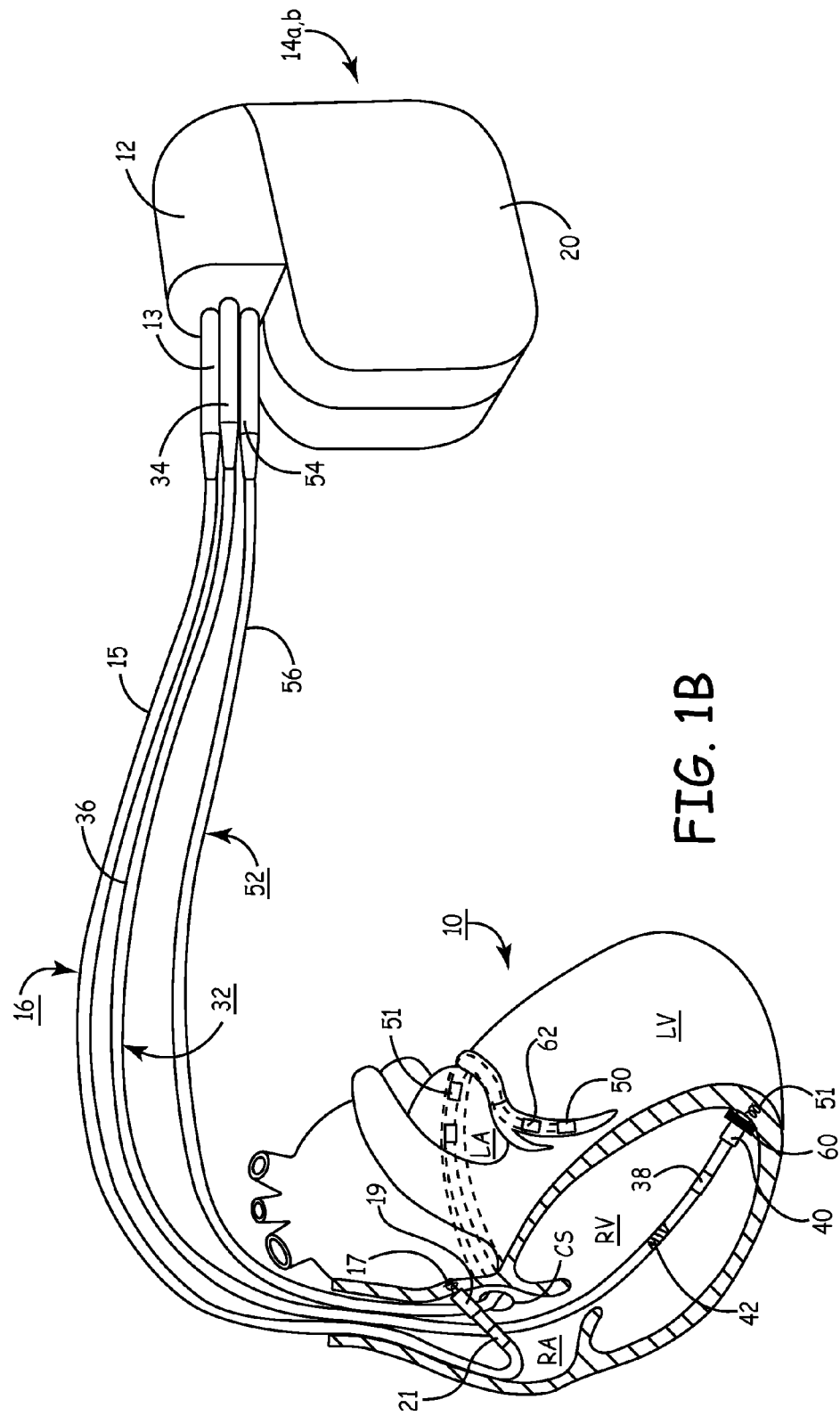
FIG. 1B depicts an implantable, multi-chamber cardiac pacemaker coupled to a patient's heart via transvenous endocardial lead.
Figure 1C:
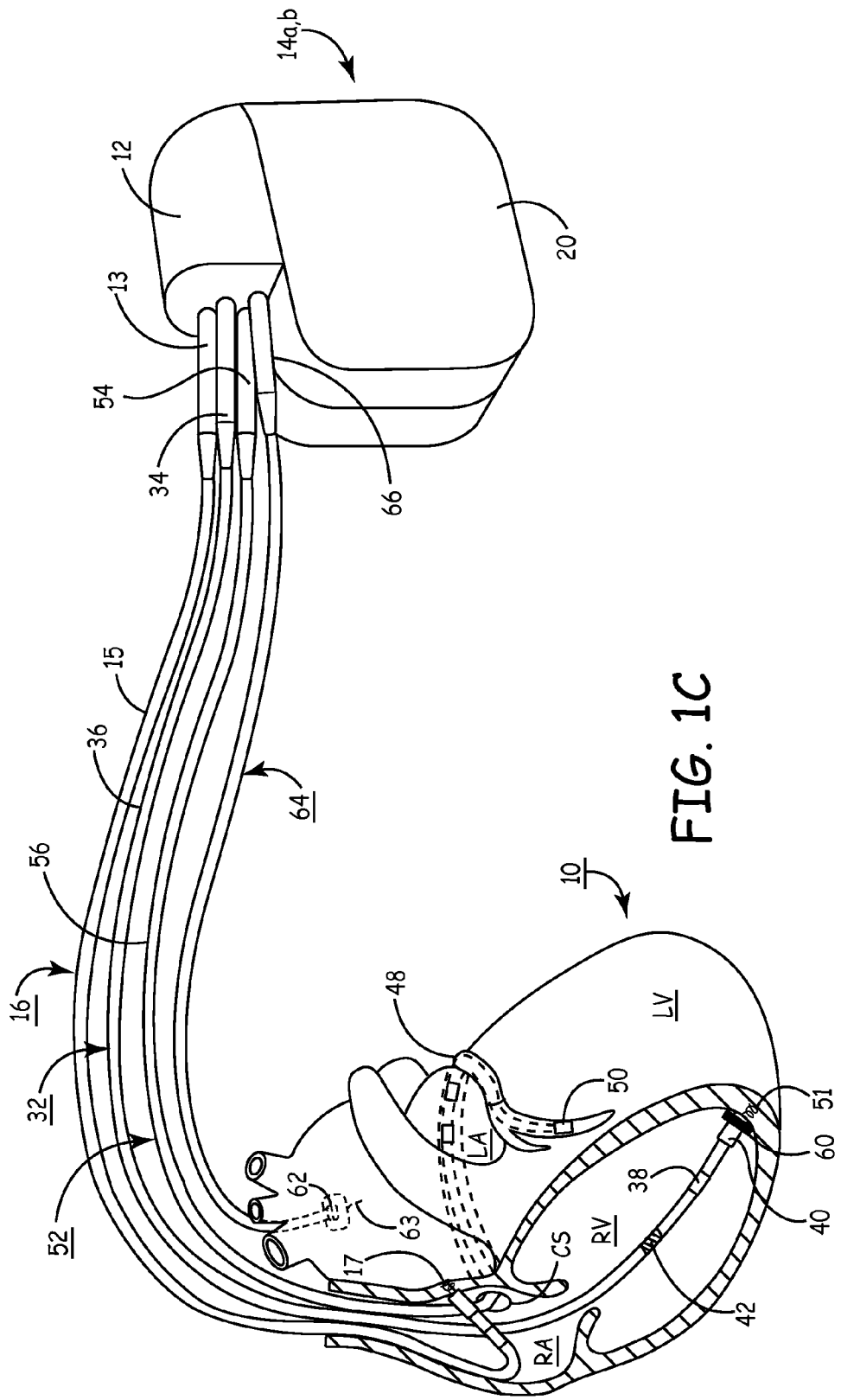
FIG. 1C depicts an implantable, multi-chamber cardiac pacemaker coupled to a patient's heart via transvenous endocardial lead.
Figure 3:
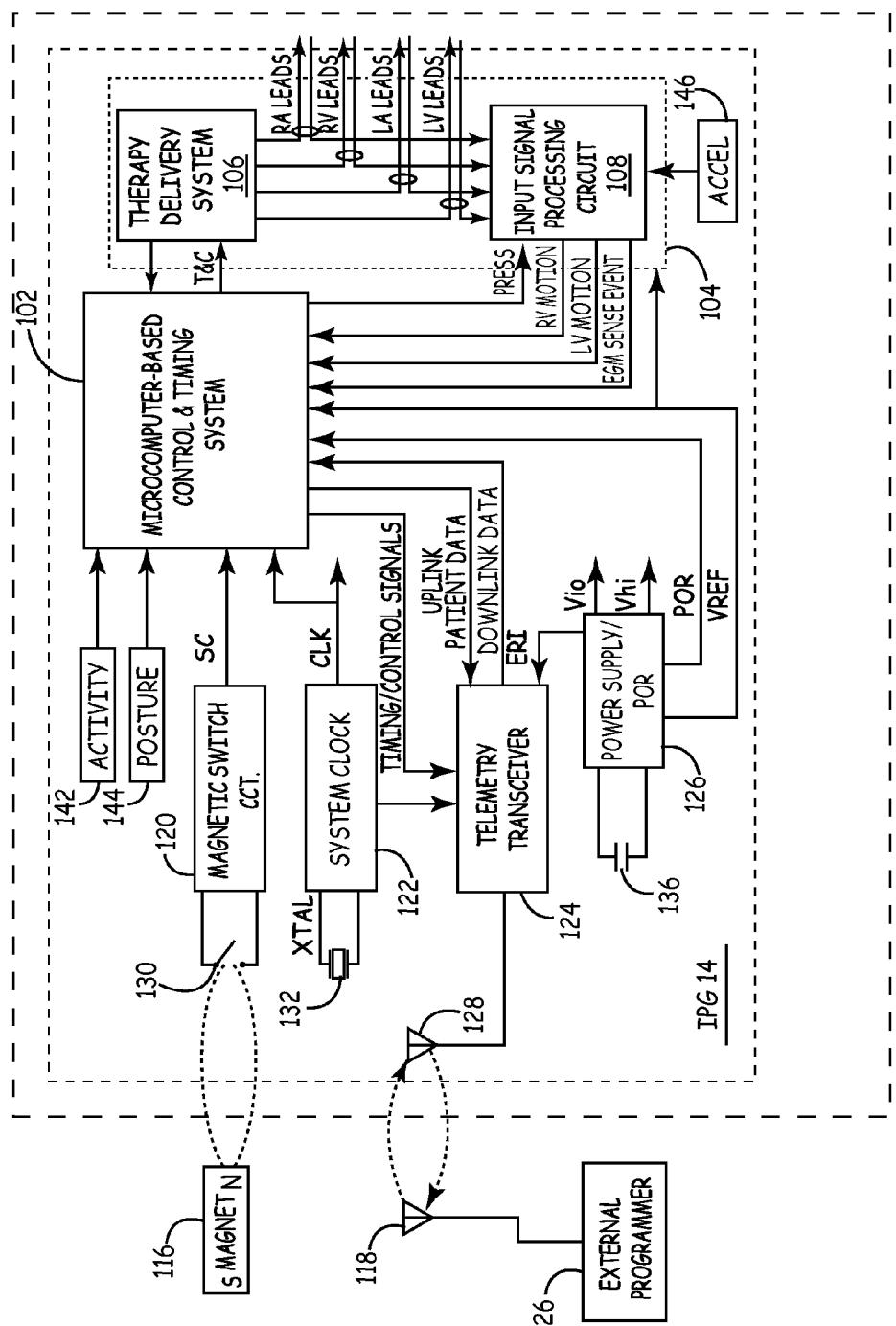
FIG. 3 is a schematic block diagram illustrating one embodiment of an implantable medical device.
Figure 4:
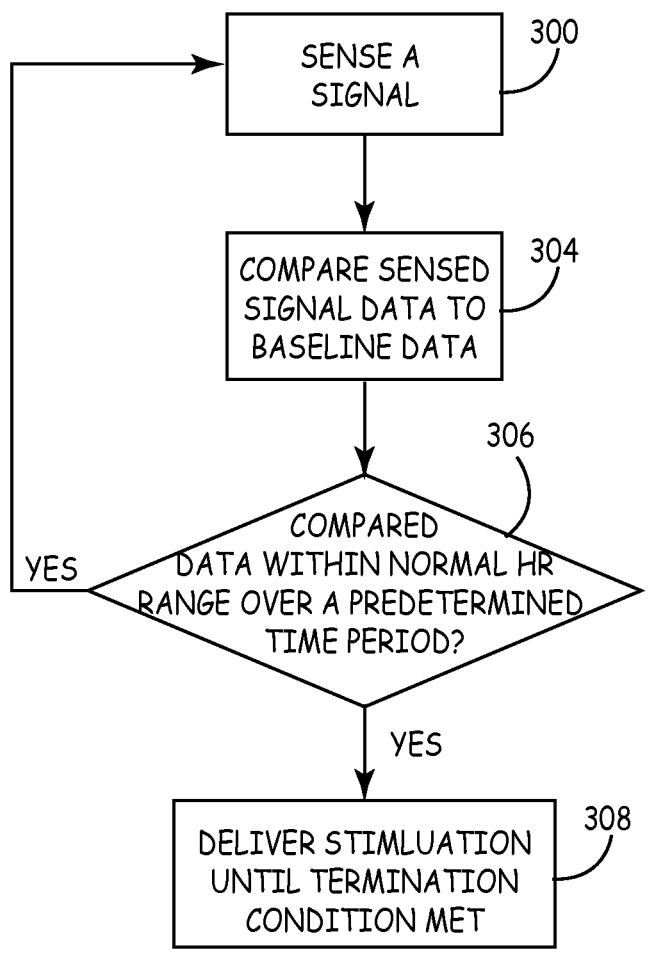
FIG. 4 is a flow diagram summarizing steps performed in a method for determining whether a patient exhibits abnormally high heart rate for a predetermined amount of time.

FIGS. 1A-1C, and 3 generally depict implantable medical device hardware embodiments, and FIG. 4 depicts operations performed by the hardware to monitor data undergoing aortic pacing. FIGS. 1A-1C depict several different hardware configurations for implementing features of the present disclosure. For example, FIG. 1A depicts a single lead stimulating aortic tissue while a second lead can sense/pace other tissue; FIG. 1B depicts a single lead stimulating aortic tissue while a second and third lead are used to sense cardiac signals and optionally deliver therapy (e.g. electrical stimuli, drug etc.); and FIG. 1C depicts an epicardial lead attached to the atrium with three endocardial leads configured to sense cardiac signals.

FIG. 1A depicts an implantable medical device 14a such as an implantable aortic pacer 14a with two medical electrical leads 16, 32 extending therefrom in communication with heart 10. Aortic pacer 14a can be a single chamber or a multi-chamber implantable medical device. While aortic pacer 14a is shown with two leads 16, and 32 in which lead 16 is used to pace aortic tissue and lead 32 is used to pace/sense other tissue, it is appreciated that other embodiments relate to an aortic pacer 14a operating solely with a single lead 16, 32 in which lead 16 solely paces/senses aortic tissue or lead 32 solely paces/senses aortic tissue through placement in the right ventricle (RV).

The multi-chamber aortic pacer 14a through lead 16 can sense intrinsic heart activity and deliver cardiac stimulation pulses as appropriate to aortic tissue. Aortic pacer 14a may be programmed to operate in any of a number of therapeutic stimulation modes. For example, aortic pacer 14a can be configured to deliver stimulation pulses to the aortic tissue. Pacing can be conducted in a tip to can configuration or through a local bipole configuration. The rate, intensity threshold and duration of aortic pacing can be customized to each patient. Exemplary intensity threshold can be less than 2 volts, 1 depolarization per pulse with about a ½ millisecond duration pulse width. Electrical stimulation can be delivered through lead 16 as pulses ranging from about 40 beats per minute to about 60 beats per minute. A heart failure patient, at rest, may merely require 40 beats per minute to lower the patient's heart rate to a more acceptable level or a customized target level for the patient. Delivery of electrical stimuli to aortic tissue can continue until the patient's heart rate meets a termination condition such as a customized target heart rate level and/or a normal heart rate level range for the patient. Detailed examples of determining a heart rate may be seen with respect to U.S. Pat. No. 6,529,771 issued to Kieval et al on Mar. 4, 2003, and assigned to the assignee of the present invention, the disclosure of which is incorporated by reference in its entirety herein.

A normal adult resting heart rate generally ranges from about 60 to about 100 beats a minute. Factors that can influence heart rate include activity level, fitness level, air temperature, body position such as standing up or lying down, emotional response to an event, body size, and/or drugs. Although a wide range of normal heart rate can exist, an unusually high or low heart rate can indicate an underlying problem. For example, a resting heart rate consistently above 100 beats a minute can indicate that a patient is experiencing tachycardia. Hypertensive urgency occurs with blood pressure above 220 systolic or 125 diastolic. Hypertensive emergency occurs when a diastolic blood pressure reading exceeds 130 with evidence of organ damage such as the brain (headache, confusion, intracranial hemorrhage and stroke), the kidneys (blood or protein in the urine and kidney dysfunction) and the heart (chest pain and heart attack). Malignant hypertension is a progression of hypertensive emergency in which there is clear evidence of increasing organ damage involving the brain (hemorrhage, stroke, encephalopathy, confusion and coma), the heart (heart attack; dysfunction; dissection—tearing or splitting—of the aorta, the main artery from the heart; the lungs (fluid retention and swelling, shortness of breath and cough); and kidneys (decreased urinary output as kidneys fail).

The customized target level of a heart rate for the patient may not be at a normal heart rate level compared to a patient without a cardiac condition. To illustrate, a customized target level for the heart rate may be 110 heartbeats per minute, which is above the normal heart rate level, at rest, of 60-100 heart beats per minute. Despite the customized target heart rate level exceeding the normal range for heart rate, the customized heart rate level may show a substantial improvement over the high heart rate detected over a predetermined period (e.g. 20 minutes etc.). Substantial improvement can be shown by a 10 percent improvement from an initial detection of a very high heart rate (e.g. 150 heartbeats per minute continuously detected as high for about 20 minutes) to an improved level of 135 heartbeats per minute after stimulating the aortic tissue.

In one or more other embodiments, aortic pacer 14a may be configured to stimulate the muscle tissue in the aorta (comprised of cardiac and smooth muscle) to manipulate the aorta's contractility thereby affecting its pressure and volume. In one or more embodiments, aortic pacing can be applied after ventricular activation with a timing delay that optimizes ventricular filling and ejection. By reducing cardiac afterload, ventricular filling is accelerated and cardiac output is increased without causing an increase in heart rate. In one or more embodiments, IMD 14a can extract cardiac afterload data from a sensed signal and then compare that data to a target range of cardiac afterload data stored in the memory of IMD 14a. Similar to heart rate data, target range of cardiac afterload can be customized to a patient or can be determined from a population of patients.

In one or more embodiments, lead 16, placed in the aorta, can have a sensor such as a pressure sensor, to sense high afterload and pressure gradients in the aorta. In one or more other embodiments, the sensor could also be used to measure a differential between the ventricle and aorta.

In one or more embodiments, single lead 16 can be placed into the atria or the right ventricle (RV) though an arterial lead introduction or a lateral thorocotamy. The aortic pacer 14a, also referred to herein as an "implantable medical device" or "IMD," can be implanted subcutaneously in a patient's body between the skin and the ribs. As depicted, the transvenous endocardial lead 16 connects to IMD 14a with the atria; however, as previously stated, lead 16 could also be placed in the RV. Lead 16 has at least one electrical conductor and pace/sense electrode. A remote indifferent can electrode 20 is formed as part of the outer surface of the housing of the IMD 14a. The pace/sense electrode(s) and the remote indifferent can electrode 20 can be selectively employed to provide a number of unipolar and bipolar pace/sense electrode combinations for pacing and sensing functions.

The depicted bipolar endocardial RA lead 16 is passed through a vein into the RA chamber of the heart 10, and the distal end of the RA lead 16 may be attached to the RA wall using a fixation member 17. The bipolar endocardial RA lead 16 is formed with a connector 13 fitting into a connector bore of IMD connector block 12 that is coupled to a pair of electrically insulated conductors within lead body 15 and connected with distal tip RA pace/sense electrode 19 and proximal ring RA pace/sense electrode 21 provided for achieving RA stimulation and sensing of RA electrogram (EGM) signals.

FIG. 1B depicts an implantable medical device (IMD) 14b such as an implantable, multi-chamber aortic pacer 14b in which IMD 14b can sense and/or deliver electrical stimulation to the aorta tissue and, if necessary, sense and deliver stimulation to other tissue through leads 16, 32 52 extending from implantable medical device 14b. Pacer 14b may be programmed to operate in any of a number of therapeutic stimulation modes. For example, IMD 14b may be configured for delivering cardiac resynchronization stimulation pulses, which control the heart activation sequence for restoring mechanical synchrony within or between one or more heart chambers. Reference is made, for example, to U.S. Pat. No. 6,070,101 (Struble, et al.) and U.S. Pat. No. 6,871,088 (Chinchoy), both of which patents are incorporated herein by reference in their entirety. In other embodiments, pacer 14b may deliver extra systolic stimulation pulses as needed to achieve post-extra systolic potentiation effects and thereby provide hemodynamic benefit to the patient. Reference is made to U.S. Pat. No. 5,213,098 (Bennett et al.), and U.S. Pat. No. 6,738,667 (Deno et al.), both of which patents are hereby incorporated herein by reference in their entirety. In various embodiments, pacer 14b may be configured to deliver any cardiac stimulation therapy that can be enhanced by or otherwise depends on an optimized AV delay or any other pacing timing control parameters to provide a beneficial effect. Although pacer 14b is shown as a multi-chamber pacemaker (sensing and stimulating in three or four heart chambers), it is understood that pacer 14b may be modified to operate as a dual chamber pacemaker.

FIG. 1B further shows IMD 14b in communication with a patient's heart 10 through medical electrical leads 16, 32, 52. The heart 10 is shown in a partially cut-away view illustrating the upper heart chambers, the right atrium (RA) and left atrium (LA), and the lower heart chambers, the right ventricle (RV) and left ventricle (LV), and the coronary sinus (CS) in the right atrium leading into the great cardiac vein 48, which branches to form inferior cardiac veins.

IMD 14b can also be implanted subcutaneously in a patient's body between the skin and the ribs. Three transvenous endocardial lead 16, 32 and 52 connect to IMD 14b with the RA, the RV and the LV, respectively. Each lead has at least one electrical conductor and pace/sense electrode. A remote indifferent can electrode 20 is formed as part of the outer surface of the housing of the IMD 14b. The pace/sense electrodes and the remote indifferent can electrode 20 can be selectively employed to provide a number of unipolar and bipolar pace/sense electrode combinations for pacing and sensing functions.

The depicted bipolar endocardial RA lead 16 is passed through a vein into the RA chamber of the heart 10, and the distal end of the RA lead 16 may be attached to the RA wall using a fixation member 17. The bipolar endocardial RA lead 16 is formed with a connector 13 fitting into a connector bore of IMD connector block 12 that is coupled to a pair of electrically insulated conductors within lead body 15 and connected with distal tip RA pace/sense electrode 19 and proximal ring RA pace/sense electrode 21 provided for achieving RA stimulation and sensing of RA electrogram (EGM) signals.

Bipolar, endocardial RV lead 32 is passed through the RA into the RV where its distal end, carrying tip RV pace/sense electrode 40 and ring RV pace/sense electrode 38, is fixed in place in the RV apex by a distal fixation member 41. The RV lead 32 is formed with a connector 34 fitting into a corresponding connector bore of IMD connector block 12 that is coupled to a pair of electrically insulated conductors within lead body 36 and connected with distal tip RV pace/sense electrode 40 and proximal ring RV pace/sense electrode 38 provided for RV stimulation and sensing of RV EGM signals. RV lead 32 may optionally include a sensor 60 responsive to RV wall acceleration, such as a heart sound sensor. One or more exemplary heart sound sensors may be seen with respect to U.S. Pat. No. 7,682,316 issued Mar. 23, 2010, entitled IMPLANTABLE HEART SOUND SENSOR WITH NOISE CANCELLATION, and assigned to the assignee of the present invention, the disclosure of which is incorporated by reference in its entirety herein.

RV acceleration sensor 60 may be positioned into or proximate the RV apex for detecting acceleration of the RV apical region. In other embodiments, RV acceleration sensor 60 may be disposed at other locations along the RV for sensing RV acceleration.

RV lead 32 may further include a blood pressure sensor 42. Blood pressure sensor 42 may be used for monitoring cardiac function and, in some embodiments, used in combination with either of the right or left wall acceleration signals for optimizing pacing timing control parameters. A RV blood pressure sensor and its use in monitoring cardiac function are generally described in U.S. Pat. No. 6,221,024 (Miesel, Apr. 24, 2001), hereby incorporated herein by reference in its entirety. It is understood that any combination of electrodes and physiological sensors, including, for example, pressure sensors, blood chemistry sensors, flow sensors, acoustical sensors, and impedance sensors, may be included in IMD 14b or an associated lead system. Such sensors may be used in conjunction with an accelerometer for sensing cardiac signals and optimizing cardiac pacing timing control parameters as will be described in greater detail below.

Coronary sinus lead 52 is passed through the RA, into the CS and further into a cardiac vein 48 to extend the distal LV CS pace/sense electrode 50 alongside the LV chamber to achieve LV stimulation and sensing of LV EGM signals. The LV CS lead 52 is coupled at the proximal end connector 54 into a bore of IPG connector block 12. A small diameter lead body 56 is typically selected in order to lodge the distal LV CS pace/sense electrode 50 deeply in a cardiac vein branching from the great cardiac vein 48.

In one embodiment of the present disclosure, one or more of three leads 16, 32 and 52 includes sensor 62. For example, as depicted, CS lead 52 is provided with a sensor 62 capable of generating a signal proportional to the acceleration of the left ventricular free wall. Sensor 62 may be embodied as a uniaxial, biaxial, or triaxial (or multiaxial) accelerometer contained in a capsule of a relatively small size and diameter such that it may be included in a coronary sinus lead without substantially increasing the lead diameter or impairing the ability to steer the lead to a left ventricular stimulation and sensing site. For the purposes of assessing cardiac function using an accelerometer deployed in operative relation to the left ventricle, a uniaxial accelerometer configured to generate a signal responsive to LV motion substantially along one axis, e.g. longitudinal acceleration, may be sufficient. Radial acceleration might be procured with multiaxial accelerometers to provide more detailed information about LV motion. Sensor 62 may alternatively be provided as another type of transducer such as a transducer having an optical, acoustical, piezoelectric, inductive, capacitive, resistive, or other elements which produce a variable signal proportional to ventricular acceleration or from which variations in ventricular acceleration can be derived.

Sensor 62 is located on CS lead 52 such that when CS lead 52 is positioned for LV stimulation and sensing, sensor 62 is located over the left ventricle and is typically positioned approximately over the left ventricular free wall mid-lateral to mid-basal segments. The depicted positions of the leads and electrodes shown in FIG. 1A in or about the right and left heart chambers are approximate and merely illustrate one of many possible configurations. For example, a left ventricular acceleration sensor 62 may alternatively be located on CS lead 52 such that sensor 62 is positioned along the great cardiac vein, or along any accessible inferior cardiac vein. Furthermore, it is recognized that alternative leads and pace/sense electrodes that are adapted for placement at stimulation or sensing sites on or in or relative to the RA, LA, RV, LV and/or aorta branch may be used in conjunction with the present disclosure.

The sensing apparatus 87 may further include one or more pressure sensors, posture sensors (e.g., 2-D or 3-D accelerometers), heart sound sensors, activity sensors, perfusion sensors etc. and/or the normalized ejection time % (ET/RR %) to monitor, or be able to determined through monitored data, one or more heart-related physiological parameters such as, e.g., patient posture, ejection time, stroke volume, cardiac output, pre-ejection time, filling time, E/A ratio, E/E', and E deceleration time etc.

In some embodiments, LV CS lead 52 could bear a proximal LA CS pace/sense electrode 51 positioned along CS lead body 56 such that it is disposed proximate the LA for use in stimulating the LA and/or sensing LA EGM signals. In that case, the lead body 56 would encase an insulated lead conductor extending proximally from the more proximal LA CS pace/sense electrode(s) and terminating at lead connector 54.

FIG. 1C depicts an implantable, multi-chamber cardiac pacemaker coupled to a patient's heart via transvenous endocardial leads and an additional left ventricular epicardial lead equipped with acceleration sensor 62. Patients may have previously had a transvenous lead system implanted that includes a coronary sinus lead 52 that is not equipped with an acceleration sensor. Such patients may benefit from the placement of an epicardial lead 64 equipped with an acceleration sensor 62 coupled to IMD 14 via a connector 66. As shown, epicardial lead 64 is connected to a surface of the aorta for pacing the aorta.

Epicardial lead 64 is provided with a fixation member 63 which may serve additionally as a pacing and/or sensing electrode. In some cases, an epicardial lead may be preferred over placing a lead into the atria through a relatively small cardiac vein. Placement of some leads can be a cumbersome task due to the tortuosity of the cardiac veins. Therefore, it may be desirable, at least in some patients, to provide an epicardial lead that can be positioned on the surface of the atrial wall for stimulation, EGM sensing and acceleration sensing, thereby eliminating the need for an endocardial lead. Alternatively, it may be desirable to deploy a small diameter lead for atrial stimulation and EGM sensing with a separate LV epicardial lead positioned for sensing LV acceleration.

The embodiment generally shown in FIG. 1C may be used for specific selection of cardiac stimulation/sensing sites. With epicardial lead 64 fixed at a desired location, the effect of pacing and/or sensing at different locations in one or more heart chambers can be evaluated by deploying the transvenous pacing leads 16, 32 and 52 to different locations. In particular, coronary sinus lead 52 may be advanced to different locations until an optimal location is identified based on analysis of the signal from LV acceleration sensor 62

Figure 2:
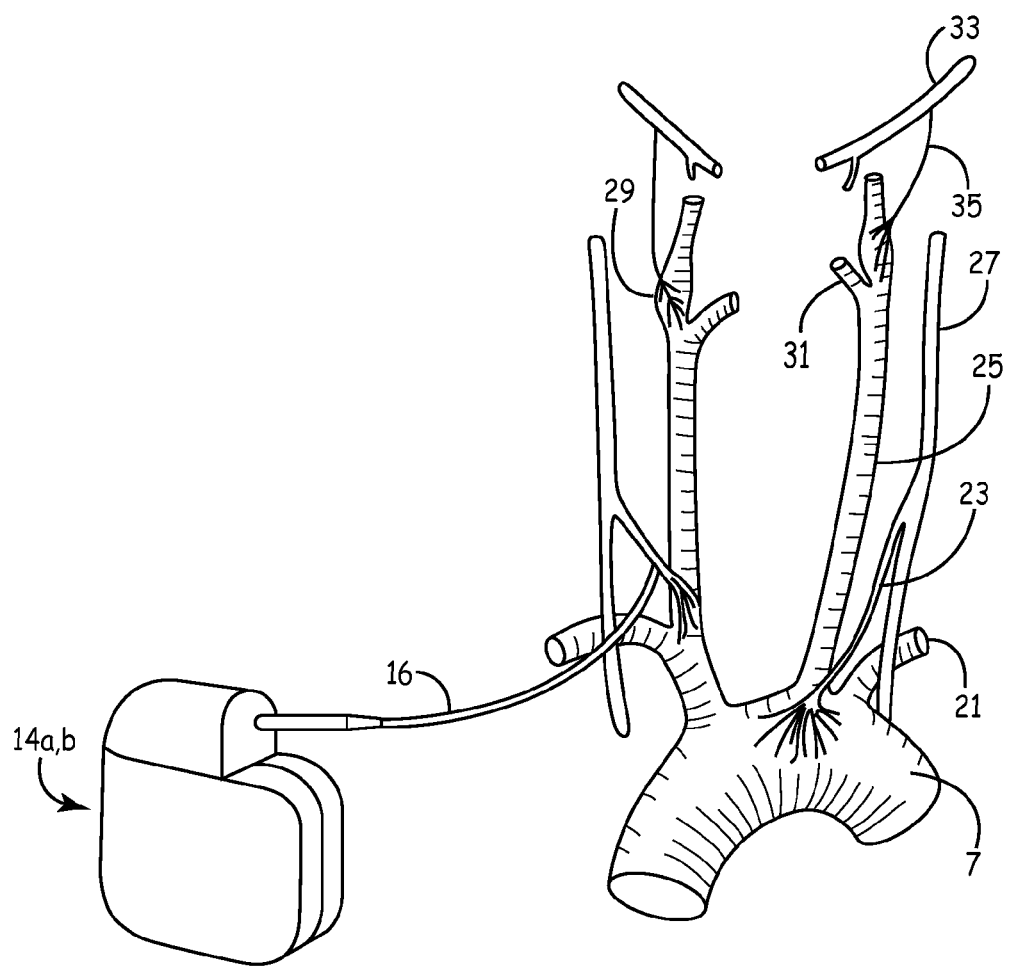
FIG. 2 is schematic diagram depicting a medical electrical lead in proximity to the aortic nerve.

FIG. 2 illustrates another embodiment for reducing heart rate through a medical electrical lead 16 directly connected or placed in close proximity to the aortic nerve 23 or cardiac baroreceptors. Baroreceptors are sensors located in blood vessels that detect the pressure of blood flowing therethrough, and can send messages to the central nervous system to increase or decrease total peripheral resistance and cardiac output. The receptors function by detecting the amount a blood vessel wall stretches, and sending a signal to the nervous system in response to the detected expansion of the vessel. Baroreceptors act as part of a negative feedback system called the baroreflex that returns blood pressure to a normal level as soon as there is a deviation from a typical pressure, such as, e.g., the mean arterial blood pressure. An example of transvascular lead placement and technique may be seen with respect to U.S. patent application Ser. No. 12/433,809 filed Apr. 30, 2009, and assigned to the assignee of the present invention, the disclosure of which is incorporated by reference in its entirety herein. After a placement location is determined, one or more leads including one or more electrodes may be deployed through the vessel wall and anchored to the vessel wall or other tissue near the target nerve tissue.

Aortic nerve 23 is substantially parallel to carotoid artery 25 and inferior to external carotoid artery 31, glossopharyngeal nerve 33, and carotoid sinus nerve 35. The aortic nerve 23 extends from the vagus nerve 27 proximate to the arch of the aorta 7 and subclavain artery 24. In this embodiment, lead 16 is connected to or in close proximity to the aortic nerve 23. In one or more embodiments, after a patient's heart rate is determined to be too high (i.e. exceeds a customized target level for a patient, above normal range for a patient, etc.), electrical stimuli can be delivered from medical electrical lead 16 to aortic nerve 23 and/or cardiac barorceptors in proximity of the aortic nerve 23. Electrical stimulation can continue until a termination condition is met. One termination condition is that the heart rate is within a target level range for the patient. Another termination condition that is checked is whether reduced efficacy has occurred to electrical stimuli such that the patient's heart rate begins to return to a higher heart rate. For example, electrical stimulation of the aortic nerve may continue until it is determined that habituation (i.e. decrease in responsiveness upon repeated exposure to an electrical stimulus, tolerance to effect of stimulation, or diminished efficacy of nerve stimulation) has occurred. When habituation has occurred, electrical stimuli can be ceased for a predetermined amount of time (e.g. 30 seconds, 10 seconds, 5 seconds, etc.). It may be preferable to cease stimulation for 5 seconds. After electrical stimulation has ceased, and if monitoring for the patient's heart rate indicates that the patient's heart rate remains higher than the target heart rate stored in the memory of IMD 14 electrical stimulation of the aortic nerve 23 and/or cardiac baroceptors is again initiated. In one or more embodiments, electrical stimulus continues until one of the termination conditions are met. In one or more embodiments, electrical stimulus continues until both termination conditions are met.

FIG. 3 is a schematic block diagram illustrating one embodiment of a multi-chamber IMD 14. IMD 14 is configured to provide a cardiac stimulation therapy and for processing a left ventricular acceleration signal input from any of the types of transducers described above or any other type of transducer sensitive to ventricular acceleration for use in optimizing pacing timing control parameters to achieve an optimized cardiac function metric.

As shown, IMD 14 includes a microprocessor-based control and timing system 102 for controlling the functions of IMD 14 by executing firmware and programmed software (or computer instructions) algorithms stored in associated memory such as RAM and ROM. Preferably, computer instructions for performing the method of detecting and/or delivering therapy for a high heart rate are stored in RAM. Control and timing system 102 may also include a watchdog circuit, a DMA controller, a block mover/reader, a CRC calculator, and other specific logic circuitry coupled together by on-chip data bus, address bus, power, clock, and control signal lines in paths or trees in a manner known in the art. It will also be understood that control and timing functions of IMD 14 can be accomplished with dedicated circuit hardware or state machine logic rather than a programmed microcomputer.

The IMD 14 includes interface circuitry 104 for receiving signals from sensors and pace/sense electrodes located at specific sites of the patient's heart chambers and delivering cardiac stimulation aimed at achieving a therapeutic benefit. The interface circuitry 104 therefore includes a therapy delivery system 106 intended for delivering cardiac stimulation pulses under the control of control and timing system 102. Delivery of stimulation pulses in one or more heart chambers is controlled in part by the selection of programmable timing intervals, which can include atrial-atrial (A-A), atrial-ventricular (A-V), and ventricular-ventricular (V-V) intervals and may further include extra systolic intervals or other timing intervals to one or more chambers according to the type of therapy being delivered and the programmed operating mode.

Physiologic input signal processing circuit 108 is provided for receiving cardiac electrogram (EGM) signals for determining a patient's heart rhythm. Physiologic input signal processing circuit 108 additionally receives signals from left ventricular acceleration sensor 62, and RV acceleration sensor 60 and RV pressure sensor 42 when used, processes these signals and provides signal data to control and timing system 102 for further signal analysis. For purposes of illustration, a set of lead connections are depicted for making electrical connections between the therapy delivery system 106 and the input signal processing circuit 108 and sets of pace/sense electrodes, acceleration sensors, and any other physiological sensors located in operative relation to the RA, LA, RV and LV.

Control and timing system 102 controls the delivery of cardiac stimulation pulses at selected timing intervals intended to improve heart function or otherwise alleviate a heart condition as needed. Selection of the programmable intervals includes an analysis of a wall acceleration signal obtained from LV acceleration sensor 62 as will be described in greater detail below. In particular, a ventricular wall acceleration signal is analyzed according to user-selected optimization criteria to optimize pacing timing control parameters, such as AV, AA and VV delays. An AV delay may be controlled by controlling a timed escaped interval following a right atrial or left atrial pacing pulse or sensed depolarization and a subsequent ventricular pacing pulse delivered in either the right or left ventricle. An AA delay may be used to control the relative timing between depolarizations of the right and left atria. Likewise, a VV delay may be used to control the relative timing between depolarizations of the right and left ventricles.

The methods described herein for optimizing a pacing timing parameter using a LV accelerometer signal may be applied to any timing parameter used to control the delivery of any pacing therapy. Accordingly, leads in communication with the patient's heart could additionally include high-voltage cardioversion or defibrillation shock electrodes.

A battery 136 provides a source of electrical energy to power components and circuitry of IMD 14 and provide energy for delivering electrical impulses to the heart. The typical energy source is a high energy density, low voltage battery 136 coupled with a power supply/POR circuit 126 having power-on-reset (POR) capability. The power supply/POR circuit 126 provides one or more low voltage power (Vlo), the POR signal, one or more reference voltage (VREF) sources, current sources, an elective replacement indicator (ERI) signal, and, in the case of a cardioversion/defibrillator capabilities, high voltage power (Vhi) to the therapy delivery system 106. A power supply and interconnections with IMD 14 components may correspond to configurations known in the art.

Electronic IMD circuitry typically employs clocked CMOS digital logic ICs that require a clock signal CLK provided by a piezoelectric crystal 132 and system clock 122 coupled thereto as well as discrete components, e.g., inductors, capacitors, transformers, high voltage protection diodes, and the like that are mounted with the ICs to one or more substrate or printed circuit board. In FIG. 3, each CLK signal generated by system clock 122 is routed to all applicable clocked logic via a clock tree. The system clock 122 provides one or more fixed frequency CLK signal that is independent of the battery voltage over an operating battery voltage range for system timing and control functions and in formatting uplink telemetry signal transmissions in the telemetry I/O circuit 124.

The RAM registers included in microprocessor-based control and timing system 102 may be used for storing data compiled from sensed EGM signals, acceleration signals, and/or relating to device operating history or other sensed physiologic parameters for uplink telemetry transmission upon receipt of a retrieval or interrogation instruction via a downlink telemetry transmission. Criteria for triggering data storage can be programmed via downlinked instructions and parameter values.

Physiologic data, including ventricular acceleration data and data derived therefrom, may be stored on a triggered or periodic basis or by detection logic within the physiologic input signal processing circuit 108.

In some cases, the IMD 14 includes a magnetic field sensitive switch 130 that closes in response to a magnetic field, and the closure causes a magnetic switch circuit 120 to issue a switch closed (SC) signal to control and timing system 102 which responds in a magnet mode. For example, the patient may be provided with a magnet 116 that can be applied over the subcutaneously implanted IMD 14 to close switch 130 and prompt the control and timing system to deliver a therapy and/or store physiologic data. Event related data, e.g., the date and time and current pacing parameters, may be stored along with the stored physiologic data for uplink telemetry in a later interrogation session.

Uplink and downlink telemetry capabilities are provided to enable communication with either a remotely located external medical device or a more proximal medical device on or in the patient's body. Stored EGM, or ventricular wall acceleration data as well as real-time generated physiologic data and non-physiologic data can be transmitted by uplink RF telemetry from the IMD 14 to the external programmer or other remote medical device 26 in response to a downlink telemetered interrogation command. As such, an antenna 128 is connected to radio frequency (RF) transceiver circuit 124 for the purposes of uplink/downlink telemetry operations. Telemeteric communication of both analog and digital data between antenna 128 and an external device 26, also equipped with an antenna 118, may be accomplished using numerous types of telemetry systems known in the art for use in implantable devices.

In accordance with one embodiment of the present disclosure, a clinician or other user uses external programmer 26 to program a selected optimization metric for use in an automatic determination of an optimal pacing timing control parameter. As will be described in greater detail below, a user interacting with external programmer may provide programming commands to IMD 14 during downlink telemetry indicating a heart rate, diastolic, systolic or combination of diastolic and systolic optimization metrics to be used by IMD 14 in executing timing parameter optimization algorithms.

The physiologic input signal processing circuit 108 includes at least one electrical signal amplifier circuit for amplifying, processing and in some cases detecting sense events from characteristics of the electrical sense signal or sensor output signal. The physiologic input signal processing circuit 108 may thus include a plurality of cardiac signal sense channels for sensing and processing cardiac signals from sense electrodes located in relation to a heart chamber. Each such channel typically includes a sense amplifier circuit for detecting specific cardiac events and an EGM amplifier circuit for providing an EGM signal to the control and timing system 102 for sampling, digitizing and storing or transmitting in an uplink transmission. Atrial and ventricular sense amplifiers include signal processing stages for detecting the occurrence of a depolarization associated with a P-wave or R-wave, respectively, and providing an atrial sense or ventricular sense event signal to the control and timing system 102. Timing and control system 102 responds in accordance with its particular operating mode to deliver or modify a stimulation therapy, if appropriate, or to accumulate data for uplink telemetry transmission in a variety of ways known in the art. Cardiac stimulation pulse delivery is generally determined based on EGM signal input according to the particular operating mode in effect. However, the intervals at which stimulation pulses are delivered may be determined, at least in part, based on an assessment of ventricular wall acceleration data as will be described below.

As such, input signal processing circuit 108 further includes signal processing circuitry for receiving, amplifying, filtering, averaging, digitizing or otherwise processing the LV wall acceleration sensor signal that can provide useful physiologic data. Acceleration signal processing circuitry is further provided for detection and/or determination of one or more acceleration signal characteristics such as maximum and minimum peak amplitudes, slopes, integrals, or other time or frequency domain signal characteristics that may be used as metrics of cardiac function. Acceleration data from an LV wall acceleration sensor signal are made available to control and timing system 102 via LV MOTION signal line. LV acceleration data may be used for monitoring cardiac function and is used in algorithms performed for identifying AV timing intervals which meet user-selected optimization criteria. If an RV acceleration sensor is present, an additional RV MOTION signal line provides RV acceleration signal data to control and timing system 102. A PRESSURE signal line provides blood pressure data received from a blood pressure sensor, which may be placed in any of the chambers of the heart or along the circulation system, to control and timing 102.

IMD 14 may further include sensors incorporated in or on the IMD housing. An activity sensor 142 provides a signal to control and timing system 102 responsive to the level of patient activity. A posture sensor 144 provides a signal to control and timing system 102 responsive to the patient's posture. Activity sensor 142 and posture sensor 144 may be used by control and timing system 102 in controlling IMD functions, for example in controlling the delivery of pacing therapies according to a patient's metabolic need and/or posture. According to some embodiments of the present disclosure, activity sensor 142 and posture sensor 144 may be used in verifying stable conditions required for performing timing parameter optimization using an LV acceleration signal. The use of activity sensors in implantable cardiac stimulation devices for determining a level of patient activity and/or providing rate-responsive pacing is known in the art. A posture sensor for use in an implantable medical device is generally described in U.S. Pat. No. 6,044,297 (Sheldon, et al.), hereby incorporated herein by reference in its entirety.

An auxiliary accelerometer 146 may be provided in or on the IMD housing and coupled to input signal processing circuit 108 for use in correcting an LV (or RV) accelerometer signal for noise. Auxiliary accelerometer 146 may be included in an implanted system and positioned at any non-cardiac location to provide a signal that may be used to adjust the LV acceleration signal to remove or minimize the effects of gravity, postural changes, patient activity, or any other non-cardiac acceleration signal sources.

IMD 14 along with the accelerometers is configured to monitor diastolic phases. During normal cardiac function, the left ventricle fills during two diastolic phases, a passive filling phase and an active filling phase. The passive filling phase occurs first as the ventricle relaxes following ventricular systole. Ventricular relaxation causes pressure within the left ventricle to fall, allowing the mitral valve between the left atrium and left ventricle to open. Blood flows into the left ventricle through the left atrium during the passive filling phase due to a pressure difference across the mitral valve. As the passive filling rate slows, the left atrium contracts, actively contributing to ventricular filling. The force generated by the actively contracting left atrium forces more blood into the ventricle. Atrial contribution to ventricular filling helps to maintain an adequate preload for ventricular contraction. According to the Frank-Starling law, the ventricles contract more forcefully during systole when filled to a greater degree during diastole.

Diastole is a period between contractions of the atria or the ventricles during which blood enters the relaxed chambers from the systemic circulation and the lungs. Ventricular diastole begins with the onset of the second heart sound and ends with the first heart sound. Systole relates to the contraction, or period of contraction, of the heart, especially of the ventricles.

Generally, cardiac stroke volume increases as cardiac filling increases. During many disease states or during various physiologic conditions such as exercise, an overlap between the phases of active atrial contraction and passive left ventricular filling can occur. Overlap between the phases of active atrial contraction and passive left ventricular filling can result in reduced atrial contribution to ventricular filling as the pressure gradient across the mitral valve is reversed from normal upon the onset of systole. This contributes to aphysiologic conditions including mitral regurgitation and flow reversal through the pulmonary vein, manifesting itself with a clinical symptom referred to as "pacemaker syndrome". If atrial contraction occurs too late after the passive filling phase, ventricular contraction may have already begun, closing the mitral valve. Late atrial contraction may cause the atria to contract against a closed or partially closed valve, which can result in retrograde flow. Early atrial contraction, prior to the end of the passive filling phase, results in fusion of the passive and active filling phases. The force available from the contracting atria can be under-utilized when blood is forced into an empty or only partially filled ventricle, which reduces the overall filling of the left ventricle and can result in reduced effectiveness of systolic contraction.

While FIGS. 1-2 and the accompanying text describe IMD 14, 14a, and 14b configured to sense electrical activity of a selected organ via one or more signals that may be monitored (e.g., using electrodes, mechanical sensor) from locations in or around a selected organ (heart, kidneys etc.), FIG. 4 is a flow diagram summarizing steps performed in a method for determining whether a patient may benefit from aortic pacing.

At operation 300 of FIG. 4, a signal is sensed through a sensor (e.g. heart sound sensor etc.) coupled to a lead and/or housing of an implantable medical device 14, 14a, or 14b. The sensed signal is transmitted to the microprocessor 102 to undergo signal processing. Exemplary techniques for decomposing a signal can include techniques as presented in Signal Processing & Linear Systems, B. P. Lahti 1998), which is incorporated by reference herein. Signal processing parses a signal into data.

At operation 304, the signal or data from the signal, is compared to a baseline signal and/or baseline data stored in memory (e.g. RAM). Exemplary baseline data can be customized to a particular patient and/or determined through averaging data over a relevant population of patients. Detection of a high heart rate is accomplished by comparing data, obtained through one or more sensors on the IMD or lead, to baseline data stored in the memory of the IMD. To illustrate, baseline data can be obtained when the patient undergoes monitoring. The baseline data from a patient may be equivalent to that of a healthy patient. Alternatively, the baseline data from patient may have a status that is less than healthy since HF patients may receive the IMD 14 after their health has deteriorated, which may not be the same or similar to the baseline data for a healthy patient. In the latter case, the baseline data may not be at an optimal value level. After the baseline data is saved in memory such as RAM, the IMD 14 can then continuously sense data through one or more sensors disposed near tissue.

At operation 306, the compared data from operation 304 is then checked against target ranges, which are stored in memory (i.e. RAM). If the compared data falls within the limitations of a desired heart rate range for the patient, then IMD 14 returns to monitoring sensed signals at block 300. If the compared data falls outside an acceptable heart rate range for a predetermined amount of time, then, at operation 308, then determination is made that therapy is to be delivered to reduce heart rate. Electrical stimulation is delivered until a termination condition is met. One termination condition occurs when the heart rate is within a target range stored in memory. Another termination condition can be predetermined. For example, electrical stimuli can continue for specified time period and then a physiological condition (e.g. heart rate, etc.) is checked.

Optionally, once a high heart rate has been determined, a notification signal can be automatically generated and wirelessly sent through an antenna on IMD 14 to a receiver or computer of a healthcare provider and/or patient.

IMD 14 continues to monitor signals from the patient to determine whether the therapy a patient's heart rate stays within an acceptable range. In one or more embodiments, IMD 14 may automatically determine that the therapy such as delivery of electrical stimuli should be adjusted (i.e. increased or decreased) in terms of the rate, intensity threshold, and duration of aortic pacing with respect to delivery of electrical stimuli. Additionally, the therapy delivered to tissue can be automatically iteratively adjusted in response to monitored signals indicating that the therapy needs to be increased or decreased. Moreover, IMD 14 can also terminate therapy delivery if it has been determined that termination condition met. A termination condition can be that the heart rate is within a predetermined healthy or improved level of health.

Thus, a method and apparatus for aortic pacing has been presented in the foregoing description with reference to specific embodiments. It is appreciated that various modifications to the referenced embodiments may be made without departing from the scope of the present disclosure as set forth in the following claims.

The invention claimed is:

1. An automated method to detect an abnormally high cardiac afterload through a chronically implanted medical device connected to a medical electrical lead, the method comprising:
sensing a signal through a sensor on the medical electrical lead, the medical electrical lead disposed along aortic arch tissue or a right ventricle (RV) of a patient;
extracting cardiac afterload data from the signal;
comparing the cardiac afterload data to a normal cardiac afterload range;
determining whether the cardiac afterload data exceeds the normal cardiac afterload range;
and delivering stimuli to the aortic arch tissue in response to determining that the cardiac afterload exceeds the normal cardiac afterload range, wherein delivery of stimuli occurs after ventricular activation with a timing delay that optimizes ventricular filling and election, and wherein the timing delay is optimized based upon a ventricular wall acceleration signal analyzed according to optimization criteria.

2. The method of claim 1 further comprising:
sensing a second signal; extracting a second cardiac afterload data from the second signal; determining the second cardiac afterload data is within an acceptable range for the patient; and terminating delivery of stimuli to the aortic arch tissue in response to determining the second cardiac afterload data is within an acceptable range for the patient.

3. The method of claim 1, wherein the medical electrical lead is placed endocardially in one of an atria and right ventricle (RV).

4. The method of claim 1, wherein the medical electrical lead is placed epicardially onto aortic arch tissue.

5. The method of claim 1, wherein the medical electrical lead is placed intravascularly to one of atria and RV.

6. The method of claim 3, wherein the cardiac afterload data indicates cardiac dysfunction.

7. The method of claim 1, further comprising:
generating a notification signal to a receiver that the cardiac afterload data is higher than the normal cardiac afterload range.

8. The method of claim 7, wherein the notification signal is transmitted to one of a healthcare provider and a patient.

9. The method of claim 1, wherein delivery of the stimuli occurs until a termination condition is met.

10. The method of claim 1, wherein delivery of the stimuli occurs for less than fifteen seconds.

11. The method of claim 1, wherein delivery of the stimuli occurs for less than ten seconds.

12. The method of claim 1, wherein delivery of the stimuli occurs for less than five seconds.

13. The method of claim 1 further comprising comparing the cardiac afterload data to baseline data, wherein the baseline data is obtained from the patient.

14. The method of claim 1 further comprising comparing the cardiac afterload data to baseline data, wherein the baseline data is based on a population of patients.

15. An automated method to detect an abnormally high cardiac afterload through a chronically implanted medical device connected to a medical electrical lead, the method comprising:
sensing a signal through a sensor on the medical electrical lead, the medical electrical lead disposed along aortic arch tissue or a right ventricle (RV) of a patient;
extracting cardiac afterload data from the signal;
comparing the cardiac afterload data to a normal cardiac afterload range;
determining whether the cardiac afterload data exceeds the normal cardiac afterload range; and
delivering stimuli to the aortic arch tissue in response to determining that the cardiac afterload data exceeds the normal cardiac afterload range,
wherein extracting cardiac afterload data from the signal comprises determining a differential pressure between a ventricle and an aorta.

16. The method of claim 1, wherein extracting cardiac afterload data from the signal comprises determining a pressure gradient in an aorta.

17. The method of claim 1, wherein delivering the stimuli comprises stimulating smooth muscle tissue in an aorta.

18. An automated method to detect an abnormally high cardiac afterload through a chronically implanted medical device connected to a medical electrical lead, the method comprising:
sensing a signal through a sensor on the medical electrical lead, the medical electrical lead disposed along aortic arch tissue or a right ventricle (RV) of a patient;
extracting cardiac afterload data from the signal;
comparing the cardiac afterload data to a normal cardiac afterload range;
determining whether the cardiac afterload data exceeds the normal cardiac afterload range; and
delivering stimuli to the aortic arch tissue to stimulate aortic muscle tissue in response to determining that the cardiac afterload data exceeds the normal cardiac afterload range, wherein the delivering of stimuli occurs after ventricular activation with a timing delay that optimizes ventricular filling and election, and wherein the timing delay is optimized based upon a ventricular wall acceleration signal analyzed according to optimization criteria.

* * * * *